United States Patent
Yadlowsky et al.

(10) Patent No.: US 9,561,085 B2
(45) Date of Patent: Feb. 7, 2017

(54) ILLUMINATED MICROSURGICAL INSTRUMENT INCLUDING OPTICAL FIBER WITH BEVELED END FACE

(71) Applicant: ALCON RESEARCH, LTD., Fort Worth, TX (US)

(72) Inventors: Michael J. Yadlowsky, Sunnyvale, CA (US); Michael James Papac, North Tustin, CA (US); Bruno Lassalas, Irvine, CA (US)

(73) Assignee: Alcon Research Ltd., Fort Worth, TX (US)

( * ) Notice: Subject to any disclaimer, the term of this patent is extended or adjusted under 35 U.S.C. 154(b) by 22 days.

(21) Appl. No.: 14/554,419

(22) Filed: Nov. 26, 2014

(65) Prior Publication Data
US 2016/0228207 A1    Aug. 11, 2016

Related U.S. Application Data

(63) Continuation of application No. 13/459,629, filed on Apr. 30, 2012, now Pat. No. 8,900,139.
(Continued)

(51) Int. Cl.
| | |
|---|---|
| A61B 1/32 | (2006.01) |
| A61M 5/14 | (2006.01) |
| G02B 6/26 | (2006.01) |
| G02B 23/24 | (2006.01) |
| A61F 9/007 | (2006.01) |

(Continued)

(52) U.S. Cl.
CPC ........... *A61B 90/30* (2016.02); *A61F 9/00763* (2013.01); *A61M 1/008* (2013.01); *A61M 5/14* (2013.01); *G02B 6/262* (2013.01); *G02B 23/2469* (2013.01); *A61B 2090/306* (2016.02); *G02B 6/04* (2013.01)

(58) Field of Classification Search
CPC ......................... A61B 90/30; A61B 2090/306
See application file for complete search history.

(56) References Cited

U.S. PATENT DOCUMENTS

| | | |
|---|---|---|
| 4,607,622 A | 8/1986 | Fritch et al. |
| 4,872,837 A | 10/1989 | Issalene et al. |
| | (Continued) | |

FOREIGN PATENT DOCUMENTS

| | | |
|---|---|---|
| AU | 741736 | 12/2001 |
| EP | 0260856 | 3/1988 |
| | (Continued) | |

OTHER PUBLICATIONS

PCT International Search Report for corresponding to PCT/US2012/035774, mailed Jul. 9, 2012, 4 pages.
(Continued)

*Primary Examiner* — Ellen C Hammond
(74) *Attorney, Agent, or Firm* — Hayes and Boone LLP

(57) ABSTRACT

An illuminated microsurgical instrument includes a microsurgical instrument having a distal tip and an optical fiber for delivering a beam of light to a surgical site. The optical fiber includes a proximal end for receiving a light beam from a light source, and a distal end proximate to the distal tip of the microsurgical instrument for emitting the light beam. The distal end includes a beveled end face either oriented toward or oriented opposite from the distal tip of the microsurgical instrument.

15 Claims, 5 Drawing Sheets

Related U.S. Application Data

(60) Provisional application No. 61/483,224, filed on May 6, 2011.

(51) Int. Cl.
    *A61M 1/00*     (2006.01)
    *G02B 6/04*     (2006.01)

(56) References Cited

U.S. PATENT DOCUMENTS

| | | | | |
|---|---|---|---|---|
| 5,201,730 | A * | 4/1993 | Easley | A61B 18/1402 604/20 |
| 5,280,788 | A | 1/1994 | Janes et al. | |
| 5,357,168 | A | 10/1994 | See | |
| 5,402,508 | A | 3/1995 | O'Rourke et al. | |
| 5,554,155 | A * | 9/1996 | Awh | A61F 9/00736 604/20 |
| 5,588,952 | A * | 12/1996 | Dandolu | A61M 1/008 362/572 |
| 5,681,264 | A | 10/1997 | Ryan, Jr. | |
| 5,785,645 | A | 7/1998 | Scheller | |
| 5,916,149 | A * | 6/1999 | Ryan, Jr. | A61B 5/0059 362/344 |
| 5,931,670 | A | 8/1999 | Davis | |
| 5,964,747 | A | 10/1999 | Eaton et al. | |
| 6,193,650 | B1 | 2/2001 | Ryan, Jr. | |
| 6,254,530 | B1 | 7/2001 | Ryan, Jr. | |
| 6,322,557 | B1 | 11/2001 | Nikolaevich et al. | |
| 6,366,726 | B1 * | 4/2002 | Wach | G01N 21/474 385/115 |
| 7,972,326 | B2 | 7/2011 | Scheller | |
| 2007/0100327 | A1 * | 5/2007 | Smith | A61F 9/007 606/4 |
| 2009/0221991 | A1 | 9/2009 | Lieponis | |
| 2011/0125139 | A1 | 5/2011 | Auld et al. | |
| 2012/0147329 | A1 * | 6/2012 | Papac | A61B 90/30 351/213 |
| 2012/0203075 | A1 * | 8/2012 | Horvath | A61B 90/30 600/249 |
| 2012/0330101 | A1 * | 12/2012 | Brennan | A61B 1/00096 600/177 |

FOREIGN PATENT DOCUMENTS

| | | |
|---|---|---|
| EP | 000651981 | 5/1995 |
| JP | S52-10346 | 4/1968 |
| JP | 05-220170 | 8/1993 |
| JP | 2002-245821 | 8/2002 |
| JP | 2007-260192 | 10/2007 |
| JP | 2011-509740 | 3/2011 |
| RU | 2130762 | 5/1999 |
| WO | WO 99/48557 | 9/1999 |
| WO | WO 03/045290 | 6/2003 |
| WO | WO 2009/091462 | 7/2009 |

OTHER PUBLICATIONS

Examination Report issued for EP Application No. 12721077.1 dated Sep. 11, 2014, 8 pages.
English Translation of Japanese Office Action issued for JP 2014-509335 dated Jan. 20, 2015 (mailing date of Jan. 27, 2015), 7 pgs.
English Translation of Office Action issued by Russian Patent Office for Application No. 2013154116/14(084558) dated Apr. 30, 2012 (mailing date of Mar. 27, 2015), 6 pages.
European Search Report and Annex to the European Search Report issued for EP Application No. 15179907 dated Nov. 13, 2015, 8 pgs.
English Translation of Korean Office Action dated Oct. 21, 2015, 5 pages.
English Translation of Decision to Grant issued for RU 2013154116 (item No. 56) dated Sep. 9, 2015, 13 pgs.
Office Communication and Search Report issued by the Taiwanese Intellectual Property Office for Taiwanese Application No. 101113000 dated Jan. 6, 2016, 6 pgs.
Office Action issued in Japanese Patent Application No. 2015-241183 issued on Nov. 1, 2016.

* cited by examiner

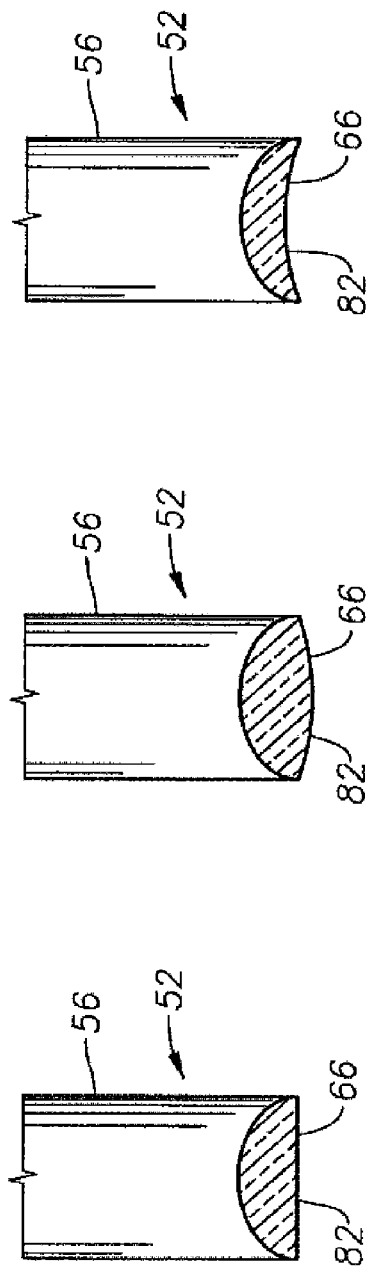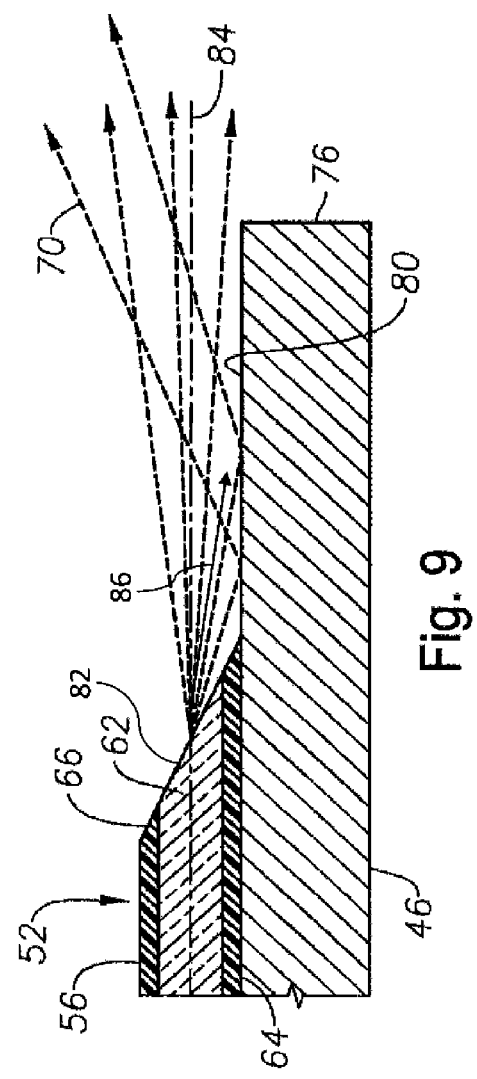

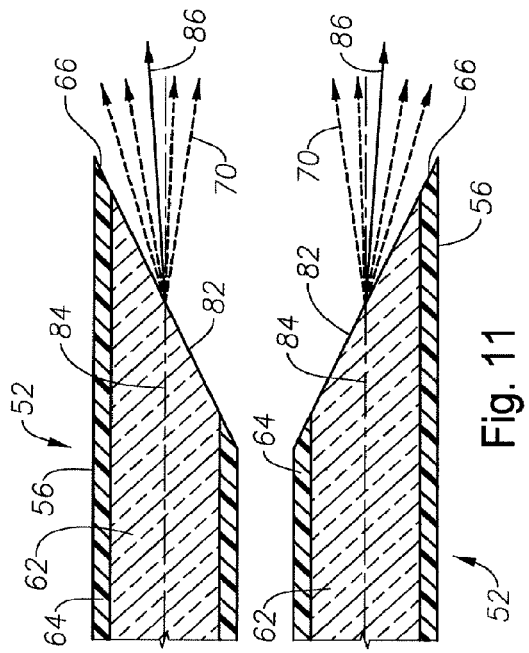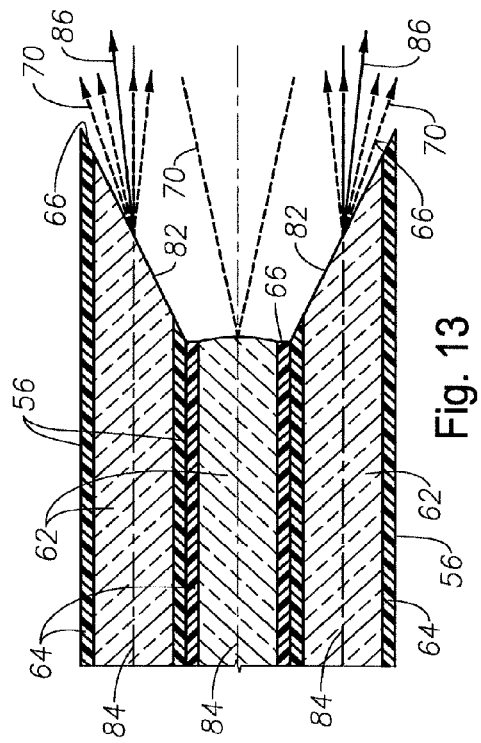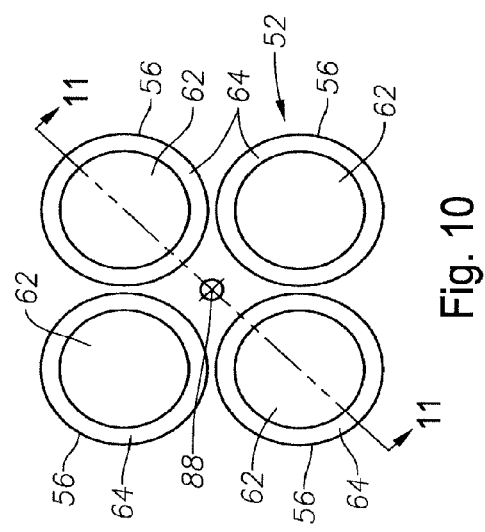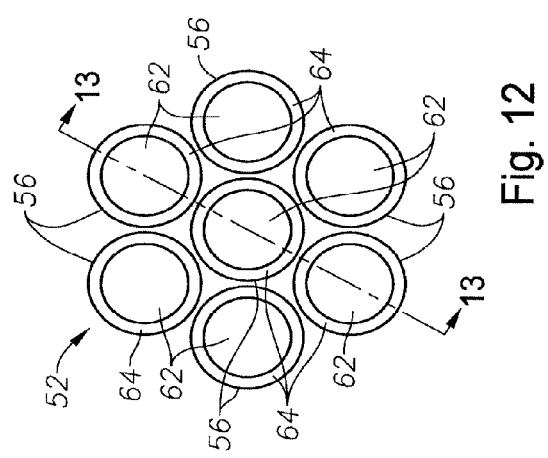

ILLUMINATED MICROSURGICAL INSTRUMENT INCLUDING OPTICAL FIBER WITH BEVELED END FACE

CROSS-REFERENCE TO RELATED APPLICATION

This application is a continuation of U.S. application Ser. No. 13/459,629 filed Apr. 30, 2012, which claims priority to and the benefit of U.S. Provisional Patent Application No. 61/483,224 filed on May 6, 2011, each of which is hereby incorporated by reference in its entirety.

BACKGROUND

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions, such as a fiber optic light source to illuminate inside the eye; an infusion line to maintain the eye's shape during surgery; and instruments to cut and remove the vitreous body. A separate incision may be provided for each microsurgical instrument when using multiple instruments simultaneously.

During such surgical procedures, proper illumination of the inside of the eye is important. Typically, a thin optical fiber is inserted into the eye to provide the illumination. A light source, such as a halogen tungsten lamp or high pressure arc lamp (metal-halides, Xe), may be used to produce the light carried by the optical fiber into the eye. The light passes through several optical elements (typically lenses, mirrors, and attenuators) and is transmitted to the optical fiber that carries the light into the eye.

As with most surgical procedures, there is a benefit to minimizing the number and size of incisions required to perform the vitreo-retinal procedure. Incisions are typically only made large enough to accommodate the size of the microsurgical instrument being inserted into the interior of the eye. Efforts to minimize the incision size generally involve reducing the size of the microsurgical instrument. Depending on the size of the microsurgical instrument employed, the incision may be small enough to render resulting wound substantially self-healing, thereby eliminating the need to employ additional procedures to close the incision, such as sutures. Reducing the number of incisions may be accomplished by integrating various microsurgical instruments. For example, the optical fiber may be incorporated into the working end of a microsurgical instrument. This may eliminate the need for a separate illumination incision, and offers the advantage of directing the light beam, together with the microsurgical instrument, onto the target site through a common opening in the sclera. Unfortunately, at least some prior attempts at integrating illuminating optical fibers with microsurgical instruments have resulted in a decrease in illuminating efficiency, or otherwise adversely effected the distribution of light emitted from the optical fibers.

BRIEF DESCRIPTION OF THE DRAWINGS

FIG. 6 is a schematic partial cross-sectional view of the fiber optic illuminator shown in FIG. 4, employing substantially planar beveled end face;

FIG. 7 is a partial cross-sectional view of the fiber optic illuminator shown in FIG. 4, employing a generally convex beveled end face;

FIG. 8 is a partial cross-sectional view of the fiber optic illuminator shown in FIG. 4, employing a generally concave beveled end face;

FIG. 9 is a schematic partial cross-sectional view of the distal end of the fiber optic illuminator, with the beveled end face arranged to face generally away from the microsurgical instrument;

FIG. 10 is a schematic end view of an alternately configured fiber optic illuminator employing multiple optical fibers;

FIG. 11 is a schematic partial cross-sectional view of the fiber optic illuminator shown in FIG. 10;

FIG. 12 is a schematic end view of an alternately configured fiber optic illuminator employing multiple optical fibers; and FIG. 13 is a schematic partial cross-sectional view of the fiber optic illuminator shown in FIG. 12.

DETAILED DESCRIPTION

Figure 1:
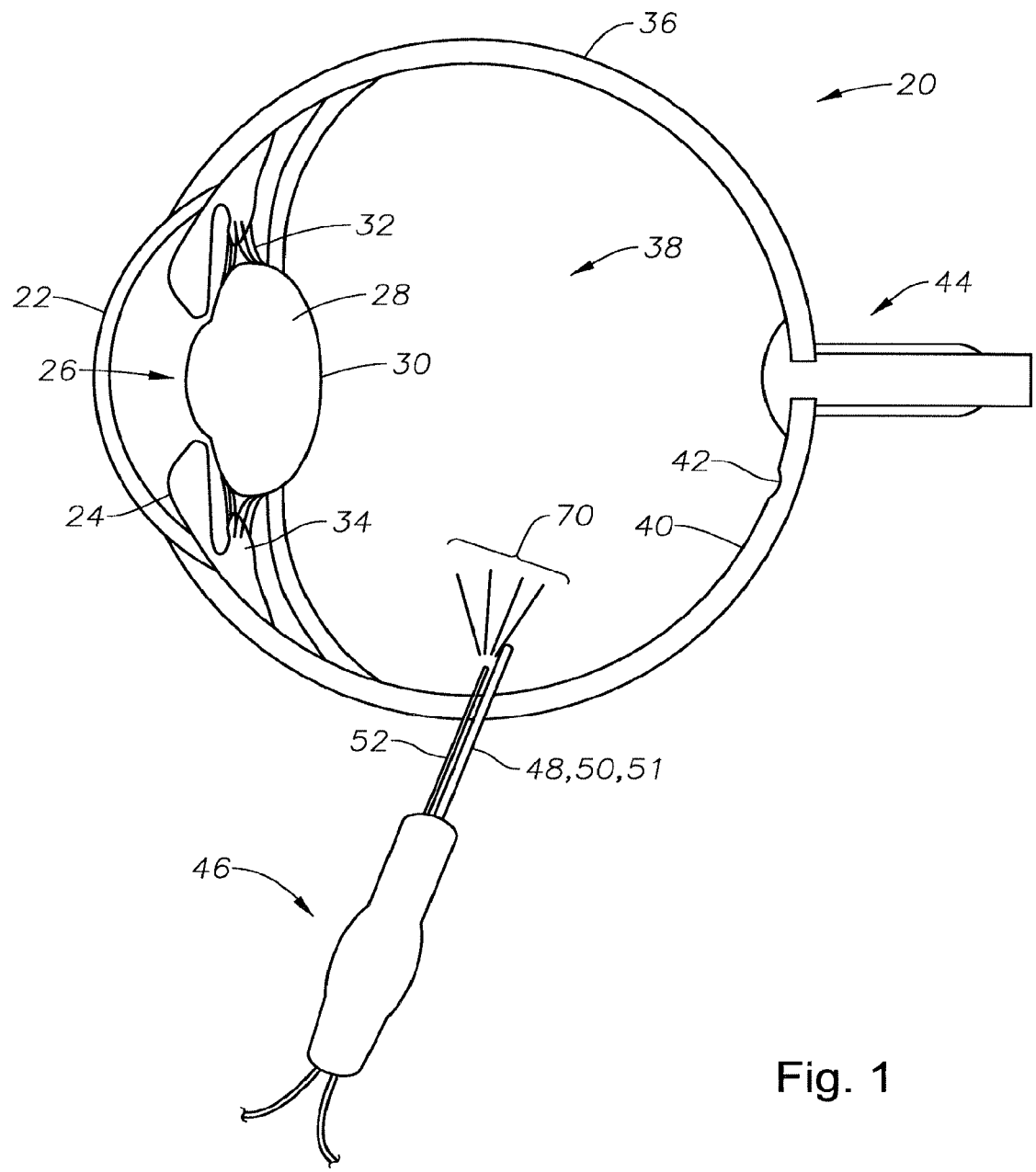
FIG. 1 is schematic illustration of an exemplary microsurgical instrument employing an exemplary integrated fiber optic illuminator, shown illuminating an interior region of an eye.

Referring now to the discussion that follows and the drawings, illustrative approaches to the disclosed systems and methods are described in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive, otherwise limit, or restrict the claims to the precise forms and configurations shown in the drawings and disclosed in the following detailed description.

FIG. 1 illustrates an anatomy of an eye 20, which includes a cornea 22, an iris 24, a pupil 26, a lens 28, a lens capsule 30, zonules 32, ciliary body 34, sclera 36, vitreous region 38, retina 40, macula 42, and optic nerve 44. Cornea 22 is a clear, dome shaped structure on the surface of eye 20 that acts as a window, letting light into the eye. Iris 24, which corresponds to the colored part of the eye, is a muscle surrounding pupil 26 that relaxes and contracts to control the amount of light entering eye 20. Pupil 26 is a round, central opening in iris 24. Lens 28 is a structure inside eye 20 that helps focus light on retina 40. Lens capsule 30 is an elastic bag that encapsulates lens 30, helping to control the shape of lens 28 as the eye focuses on objects at different distances. Zonules 32 are slender ligaments that attach lens capsule 30 to the inside of eye 20, holding lens 28 in place. Ciliary body 34 is a muscular area attached to lens 28 that contracts and relaxes to control the size of the lens for focusing. Sciera 36 is a tough, outermost layer of eye 20 that maintains the shape of the eye. Vitreous region 38 is a large, gel-filled section located towards a back of eye 20 that helps maintain the curvature of the eye. Retina 40 is a lightsensitive nerve layer at the back of eye 20 that receives light and converts it into signals to send to the brain. Macula 42 is an area in the back of eye 20 that includes receptors for detecting fine detail in a viewed image. Optic nerve 44 transmits signals from eye 20 to the brain.

With continued reference to FIG. 1, various microsurgical instruments 46 may be inserted through sclera 36 into vitreous region 38 when performing an ophthalmic surgical procedure, such as a vitreoretinal procedure. For purposes of this specification, a microsurgical instrument 46 refers to any tool sized for insertion through an incision that is adapted to perform physical or electromagnetic manipulation of ocular tissue. These may include a variety of surgical instruments, such as, for example, a vitrectomy probe 48, infusion cannula 50 and aspiration probe 51. Microsurgical instrument 46 may include an integrated fiber optic illuminator 52 for illuminating an interior of eye 20.

Figure 2:
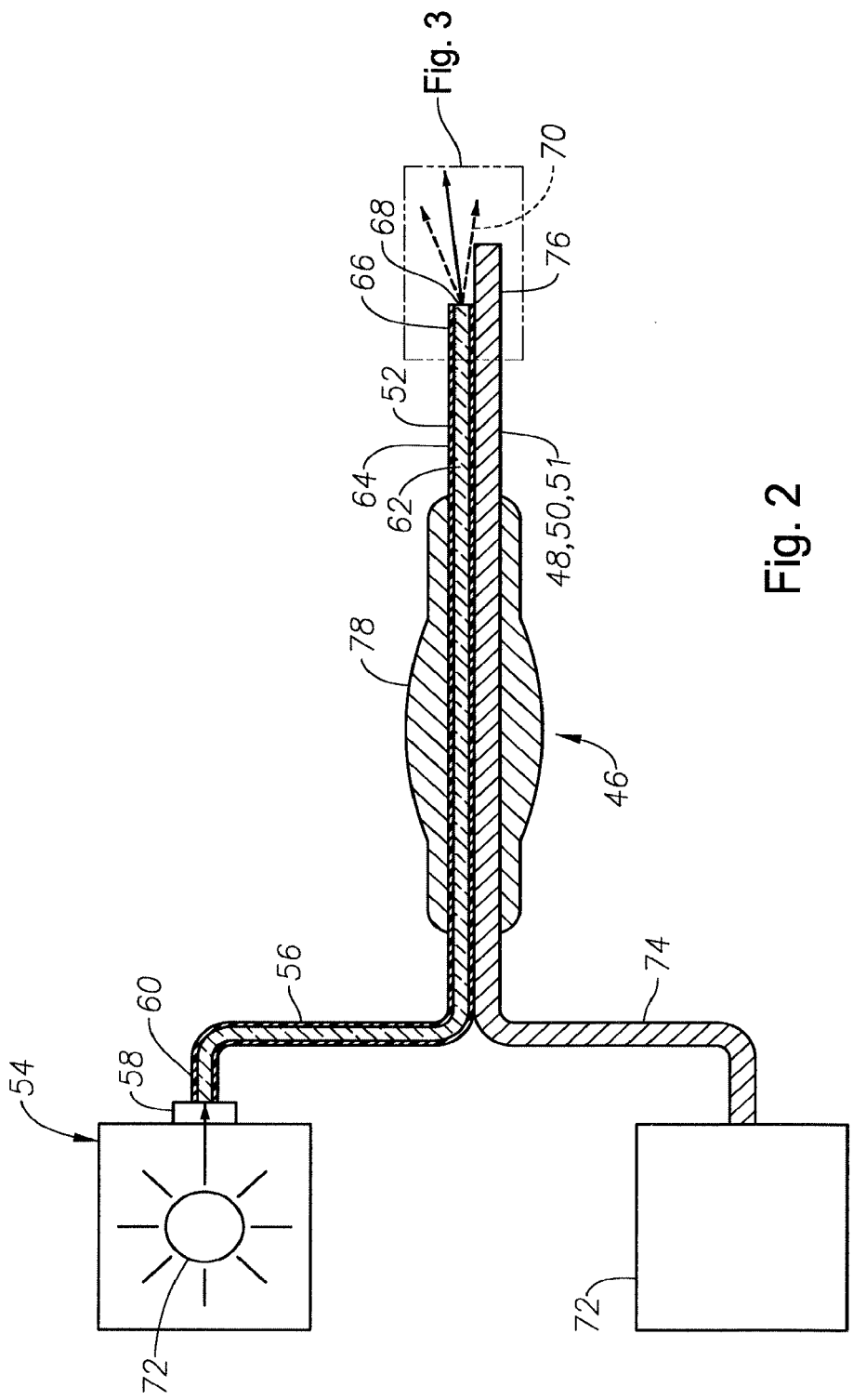
FIG. 2 is a schematic partial cross-sectional view of the microsurgical instrument and integrated fiber optic illuminator.

With reference to FIG. 2, fiber optic illuminator 48 may be optically connected to an illuminator 54 for producing light that may be used to illuminate vitreous region 38 of eye 20 during various intra-optical procedures, such as vitreoretinal surgery. Light produced by illuminator 54 may be transmitted to the interior region of the eye through an optical fiber 56. Optical fiber 56 may include a fiber optic connector 58 for optically connecting a proximal end 60 of optical fiber 56 to illuminator 54. Fiber optic connector 58 may be configured to releasably connect to a correspondingly configured illuminator optical connector operably associated with illuminator 54.

Continuing to refer to FIG. 2, optical' fiber 56 may have any of a variety of configurations. In the exemplary configuration shown in FIG. 2, optical fiber 56 includes an optically transmissive fiber optic core 62 surrounded by a cladding material 64 having a low index of refraction relative to core 62. Fiber optic core 62 may be made of various materials, including, but not limited to, glass and plastics. Optical fiber 56 may also include additional layers, depending on the requirements of a particular application. For example, optical fiber 56 may include a buffer material encasing cladding material 64, as well as an outer protective jacket for shielding the cable's interior components from damage. A distal end 66 of optical fiber 56 may include an opening 68 for emitting light 70 produced by illuminator 54.

Continuing to refer to FIG. 2, illuminator 54 may employ a light source 72 for generating light at a particular luminous flux and chromaticity. The light may be emitted over a relatively wide or narrow range of wavelengths depending on the type of light source employed. Light source 72 may employ various light producing technologies, including, but not limited to, lamp based light sources, such as halogen tungsten lamps and high-pressure arc lamps (metal-halides and Xe). Light emitting diodes (LEDs) may also be employed as light source 72. Lasers may also be employed as light source 72. Lasers are generally capable of producing light having a relatively high degree of coherence, as compared to other light sources, such as LEDs and lamp based light sources. High coherence enables the emitted light to be focused to smaller spot sizes for more efficient transmission to optical fiber 56. The ability to focus the emitted light to small spot sizes may enable the use of smaller optical fibers, such as nano-scaled optica; fibers, which may in turn limit the size of an incision required to insert microsurgical instrument 46 into eye 20. Nano-scale optic fibers generally have a diameter (or other largest cross-sectional dimension) of less than 100 microns.

Due to the small size of nano-scale optic fibers, it may be possible to integrate fiber optic illuminator 52 with another surgical instrument, such as microsurgical instrument 46, to reduce the number of surgical incisions required for inserting surgical instruments during a vitreoretinal procedure. Continuing to refer to FIG. 2, microsurgical instrument 46 may be suitably connected to a service source 72, for example, via conduit 74. Service source 72 may be configured to provide various services used in connection with operating microsurgical instrument 46. For example, Service source 72 may provide pressure and/or vacuum for operating microsurgical instrument 46. Vacuum may also be provided for aspirating fluids and materials from the interior of eye 20. Service source 72 may provide a source of fluids used in connection with the surgical procedure.

Microsurgical instrument 46 may have various configurations depending on the surgical procedure performed. For example, certain ophthalmic surgical procedures may require the cutting and/or removal of vitreous region 38, which is a transparent jelly-like material that fills the posterior segment of eye 20. Vitrectomy probe 48 may be used to resect and remove the vitreous region. In one exemplary configuration, vitrectomy probe 48 may include a hollow outer cutting member, a hollow inner cutting member arranged coaxially with and movably disposed within the hollow outer cutting member, and a port extending radially through the outer cutting member near a distal end 76 thereof. Vitreous region 38 is aspirated into the open port, and the inner member is actuated to close the port and sever the vitreous material, which may then be aspirated away through conduit 74. The mechanism for actuating the hollow inner member may be enclosed within a housing 78, which may also function as a handle for grasping microsurgical instrument 46. Microsurgical instrument 46 may also be configured as infusion cannula 50 for delivering a fluid to the interior of eye 20. The fluid may be delivered to infusion cannula 50 through conduit 74. Conduit 74 may also be used to connect microsurgical instrument 46 to a vacuum source, for example, when configuring microsurgical instrument 46 as aspiration probe 51.

Figure 3:
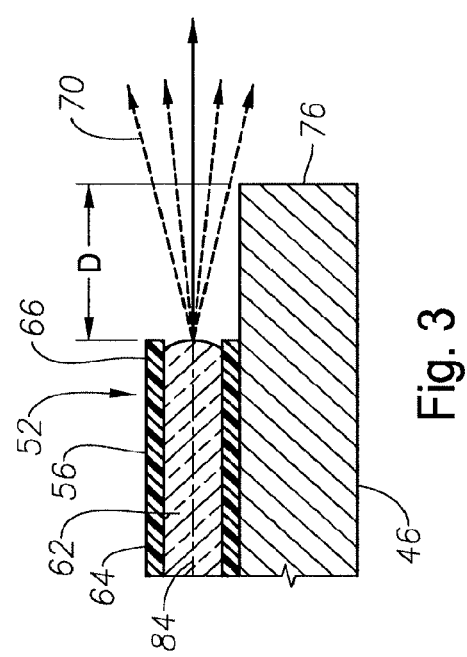
FIG. 3 is a schematic partial cross-sectional view of a distal end of the microsurgical instrument and integrated fiber optic illuminator shown in FIG. 2.

Referring to FIG. 3, in certain applications, it is generally desirable for light beam 70 emitted from fiber optic illuminator 52 to have a relatively wide angular distribution to enable illumination of a corresponding wide surgical field within eye 20. However, a portion of the light beam 70 emitted from optical fiber may be either absorbed or reflected from an adjacent outer surface 80 of microsurgical instrument 46, depending on the positioning of distal end 66 of optical fiber 56 relative to distal end 76 of microsurgical instrument 46. It may not always be desirable, however, to position distal end 66 of optical fiber 56 proximate to end 76 of microsurgical instrument 46. Positioning distal end 66 of optical fiber 56 a distance "D" from distal end 76 of microsurgical instrument 46 may, however, adversely affect the illuminating efficiency of fiber optic illuminator 52, particularly in instances in which a measurable portion of the emitted light is absorbed by outer surface 80 of microsurgical instrument 46.

Figure 4:
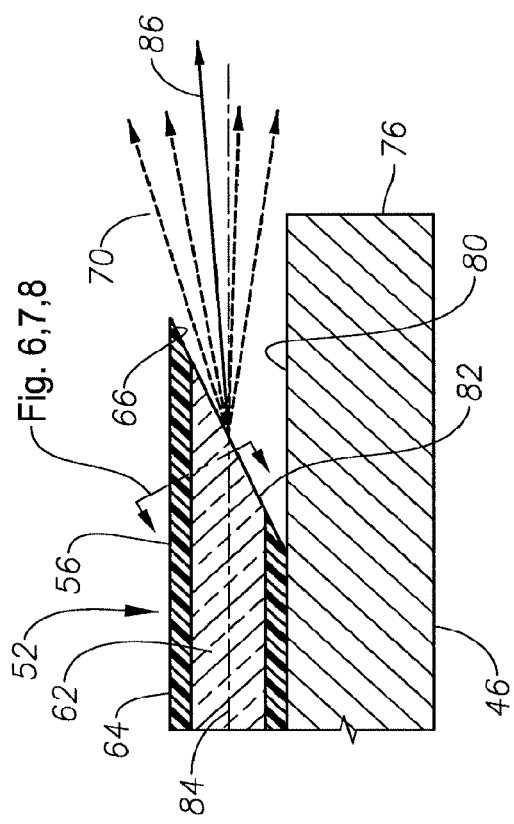
FIG. 4 is a schematic partial cross-sectional view of the distal end of the fiber optic illuminator configured to include a beveled end face.
Figure 5:
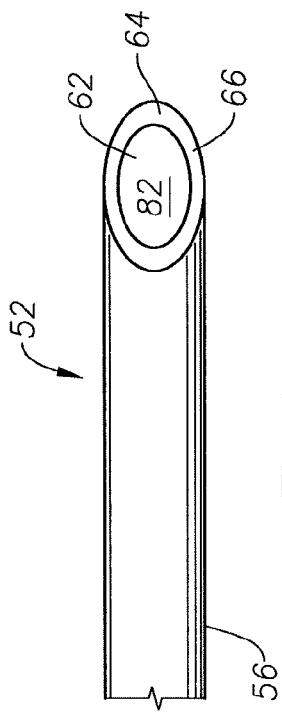
FIG. 5 is a schematic plan view of the fiber optic illuminator shown in FIG. 4.

Referring to FIGS. 4 and 5, to help avoid a distal tip of microsurgical instrument 46 interfering with the propagation of light beam 70 emitted from optical fiber 56, distal end 66 may be provided with a beveled end face 82 arranged at an oblique angle relative to an optical axis 84 of optical fiber 56. For purposes of this specification, "beveled end face" need not refer strictly to a flat beveled surface but rather may include any configuration wherein a distalmost end face is arranged so that the surface normal, i.e., the axis perpendicular to the surface, is deviated to one side of the optical axis 84 over the majority of the end face, making the distalmost end face asymmetrical relative to the optical axis. When the beveled end face 82 is said to "point" or to be "oriented" toward a certain direction, this refers to the side of the optical axis 84 toward which the beveled end face 82 is asymmetrically deviated. Inclining end face 82 relative to optical axis 84 generally results in light beam 70 approaching beveled end face 82 at an oblique incidence angle relative to the surface normal at the point of incidence. The transition between the two different refractive indices causes the light to refract as it transitions the interface between optical fiber 56 and vitreous region 38 of eye 20, thereby deflecting a propagation path 86 of light beam 70 away from optical axis 84 of optical fiber 56. The amount of refraction may be approximated using Snell's law, which provides:

$$n1 * \sin(\theta_1) = n2 * \sin(\theta_2) \text{ where:}$$

n1 is the refractive index of fiber optic core 62
n2 is the refractive index of vitreous region 38
($\theta_1$) is the propagation angle of light beam 70 within fiber optic core 62
($\theta_2$) is the propagation angle of light beam 70 within vitreous region 38,
where ($\theta_1$) and ($\theta_2$) are both measured relative to the surface normal of the beveled end face 82.

Because the index of refraction of the vitreous region is lower than that of the fiber optic core, the light beam 70 will tend to be refracted away from the surface normal of the beveled end surface 82, viz., ($\theta_2$)>($\theta_1$) The angular distribution of the rays in light beam 70 as the rays travel through the optical fiber 56 will therefore produce an angular distribution in the emitted light beam 70, which will be preferentially shifted away from the optical axis 84 of the optical fiber 56.

While beveled end face 82 is illustrated on an optical fiber 56 of uniform diameter, beveled end face 82 may also be used on a fiber optic with a tapered distal tip that narrows to a smaller width along a path that may includes curved or straight segments as the fiber optic extends toward the distal tip. In particular embodiments of the tapered distal tip, the cladding may also be removed. The tapered distal end provides a wider angular distribution, which may advantageously be combined with the deflection produced by the beveled end face 82 to produce a wider illumination beam from the fiber optic selectively directed in a particular direction around the tip of the surgical instrument.

The deflection of light beam 70 relative to microsurgical instrument 46 is at least partially dependent on the orientation of beveled end face 82 relative to microsurgical instrument 46. For example, orienting beveled end face 82 to point toward microsurgical instrument 46, such as shown in FIG. 4, tends to shift propagation path 86 of the light beam away from microsurgical instrument 46. On the other hand, orienting beveled end face 82 to point away from microsurgical instrument 46, such as shown in FIG. 9, tends to shift the propagation path 86 of light beam 70 toward microsurgical instrument 46. Referring to FIG. 9, fiber optic illuminator 52 is shown with beveled end face 82 oriented to face generally away from microsurgical instrument 46. This arrangement generally results in propagation path 86 of light beam 70 being shifted toward microsurgical instrument 46. Thus, this arrangement increases, rather than decreases, the amount of light reflected from microsurgical instrument 46. A wider dispersion of light emitted from optical fiber may be obtained by enhancing the reflectivity of outer surface 80 of microsurgical instrument 46. Light emitted from optical fiber 56 may be reflected from surface 80 of microsurgical instrument 46 to provide a broader distribution of light within an interior region of eye 20.

FIGS. 6-8 are partial cross-sectional views taken through beveled end face 82 (see FIG. 4) along a perspective generally parallel to end face 82. Beveled end face 82 may include a variety of surface contours. For example, FIG. 6 shows beveled end face 82 configured to include a planar surface. Beveled end face 82 may alternatively be configured to include a generally convex surface contour, such as shown in FIG. 7. Beveled end face 82 may also have a generally concave configuration, as shown in FIG. 8. These are merely a few examples of the various surface contours that may be employed with beveled end face 82. In practice, other contours may also be employed to accommodate design and performance requirements of a particular application.

Referring to FIGS. 10-13, fiber optic illuminator 52 may be configured to include multiple bundled optical fibers 56 surrounding a distal tip of a microsurgical instrument 46. FIG. 10 shows an exemplary arrangement including four optical fibers 56 bundled together. Each optical fiber may include a beveled end face 82 for selectively controlling a propagation path of emitted light. In the exemplary arrangement illustrated in FIGS. 10 and 11, beveled end face 82 of optical fibers 56 positioned at opposite corners of the cable bundle are shown oriented so as to generally face one another. This particular arrangement tends to increase the dispersion of the emitted light by shifting propagation path 86 of light beam 70 outward from a center axis 88 of the bundle.

FIGS. 12 and 13 show an exemplary optical fiber bundle including seven optical fibers 56. The optical fibers are shown arranged generally in a hexagonal pattern, with six optical fibers positioned around a center optical fiber. Each of the outer optical fibers 56 may include a beveled end face 82 for selectively controlling a propagation path of emitted light. The single center optical fiber 56 in this exemplary configuration does not include a beveled end face. Beveled end faces 82 of the outer optical fibers 56 may be oriented so as to generally point radially inward toward a center of the optical fiber bundle. This particular arrangement tends to increase the dispersion of the light emitted from the outer optical fibers by shifting propagation path 86 of light beam 70 outward from the center of the optical fiber bundle.

The distal end of the entire bundle is placed proximate to a distal tip of a microsurgical instrument 46. The central fiber optical cable and/or the optical fibers that are more remote from the distal tip of the microsurgical instrument 46 can have a flat surface so that the propagation path of light emitted from the center optical fiber tends to coincide with optical axis of the optical fiber. In such embodiments, light emitted from the center optical fiber 56 may fill a light void that may exist between the light beams emitted from the surrounding outer optical fibers 56, while still allowing the overall amount of reflected light from the distal tip of the microsurgical instrument 46 to be reduced by the orientation of the closest optical fibers 56. For example, if the distal tip of the microsurgical instrument 46 is reflective, then the depicted orientation of the beveled end faces 82 can advantageously provide additional illumination through reflection, as previously illustrated in FIG. 9. Alternatively, in the case of a non-reflective tip of microsurgical instrument 46, the beveled end faces 82 could be reversed to point toward the distal tip of microsurgical instrument 46, preferentially shifting the illumination away from the distal tip of microsurgical instrument 46, as illustrated in FIG. 4. In yet another alternative embodiment, the optical fibers 56 can be placed in a similar configuration as illustrated in FIGS. 10-13, but centered around the distal tip of microsurgical instrument 56, so as to produce illumination from multiple optical fibers 56 around the microsurgical instrument 56.

It will be appreciated that the exemplary surgical illumination system described herein has broad applications. The foregoing configuration were chosen and described in order to illustrate principles of the methods and apparatuses as well as some practical applications. The preceding description enables others skilled in the art to utilize methods and apparatuses in various configurations and with various modifications as are suited to the particular use contemplated. In accordance with the provisions of the patent statutes, the principles and modes of operation of the disclosed surgical illumination system have been explained and illustrated in exemplary configurations.

It is intended that the scope of the present methods and apparatuses be defined by the following claims. However, it must be understood that the disclosed surgical illumination system may be practiced otherwise than is specifically explained and illustrated without departing from its scope. It should be understood by those skilled in the art that various alternatives to the configuration described herein may be employed in practicing the claims without departing from the scope as defined in the following claims. The scope of the disclosed surgical illumination system should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the device and that the method and apparatus within the scope of these claims and their equivalents be covered thereby. In sum, it should be understood that the device is capable of modification and variation and is limited only by the following claims.

What is claimed is:

1. An illuminated microsurgical instrument, comprising:
a microsurgical instrument having a distal tip sized and shaped for insertion through an incision in a human eye and into a vitreous region of the eye; and
an optical fiber for delivering a beam of light to a surgical site of the eye coupled to the microsurgical instrument, the optical fiber including a proximal end for receiving a light beam from a light source, and a distal end proximate to the distal tip of the microsurgical instrument for emitting the light beam, the distal end including a beveled end face oriented away from the distal tip of the microsurgical instrument at an oblique angle with respect to an optical axis of the optical fiber.

2. The illuminated microsurgical instrument of claim 1, wherein:
the optical fiber has an index of refraction greater than an index of refraction of the vitreous region of the eye such that a propagation path of the light beam from the beveled end face is towards the microsurgical instrument.

3. The illuminated microsurgical instrument of claim 2, wherein:
the microsurgical instrument includes a reflective surface proximate to the distal tip.

4. The illuminated microsurgical instrument of claim 1, wherein:
the beveled end face bisects the optical axis of the optical fiber.

5. The illuminated microsurgical instrument of claim 1, wherein:
the beveled end face includes a planar surface.

6. The illuminated microsurgical instrument of claim 1, wherein:
the beveled end face includes a convex surface.

7. The illuminated microsurgical instrument of claim 1, wherein:
the beveled end face includes a concave surface.

8. The illuminated microsurgical instrument of claim 1, wherein:
the optical fiber has an outer diameter less than 100 microns.

9. The illuminated microsurgical instrument of claim 1, wherein:
the microsurgical instrument is selected from the group consisting of a vitrectomy probe, an infusion cannula, and an aspiration probe.

10. A microsurgical system, comprising:
a light source;
a microsurgical instrument having a distal tip sized and shaped for insertion through an incision in a human eye and into a vitreous region of the eye; and
an optical fiber for delivering a beam of light to a surgical site of the eye coupled to the microsurgical instrument, the optical fiber including a proximal end for receiving a light beam from the light source, and a distal end proximate to the distal tip of the microsurgical instrument for emitting the light beam, the distal end including a beveled end face oriented away from the distal tip of the microsurgical instrument at an oblique angle with respect to an optical axis of the optical fiber.

11. The microsurgical system of claim 10, wherein:
the light source includes at least one of a lamp based light source, an light emitting diode (LED) light source, or a laser source.

12. The microsurgical system of claim 10, further comprising:
a service source connected to the microsurgical instrument.

13. The microsurgical system of claim 12, wherein:
the service source includes at least one of a pressure source, a vacuum source, or a fluid source.

14. The microsurgical system of claim 10, wherein:
the optical fiber has an index of refraction greater than an index of refraction of the vitreous region of the eye such that a propagation path of the light beam from the beveled end face is towards the microsurgical instrument.

15. The microsurgical system of claim 14, wherein:
the microsurgical instrument includes a reflective surface proximate to the distal tip.

* * * * *